United States Patent [19]

Mullen

[11] Patent Number: 5,320,749
[45] Date of Patent: Jun. 14, 1994

[54] APPARATUS FOR TREATMENT OF FLUID MEDIA WITH ULTRAVIOLET IRRADIATION

[76] Inventor: Patrick J. Mullen, 929 N. Vermillion, Gary, Ind. 46403

[21] Appl. No.: 857,665

[22] Filed: Mar. 26, 1992

[51] Int. Cl.$^5$ .............................................. C02F 1/32
[52] U.S. Cl. .................... 210/199; 210/205; 210/748; 250/435; 250/437; 422/186.3
[58] Field of Search .................. 210/748, 199, 205; 250/432 R, 435–438; 422/24, 186.3

[56] References Cited

U.S. PATENT DOCUMENTS

| | | | |
|---|---|---|---|
| 3,634,025 | 1/1972 | Landry | 250/436 |
| 3,700,406 | 10/1972 | Landry | 422/24 |
| 4,101,777 | 7/1978 | Reid | 250/436 |
| 4,103,167 | 7/1978 | Ellner | 250/432 R |
| 4,471,225 | 9/1984 | Hillman | 250/436 |
| 4,676,896 | 6/1987 | Norton | 210/248 |
| 4,798,702 | 1/1989 | Tucker | 422/24 |
| 5,174,904 | 12/1992 | Smith, II | 210/748 |

OTHER PUBLICATIONS

"Ultraviolet Disinfection System", Product Specifications Brochure, Ultraviolet Systems, Inc.

Primary Examiner—Neil M. McCarthy
Attorney, Agent, or Firm—Wood, Phillips, VanSanten, Hoffman & Ertel

[57] ABSTRACT

The present invention provides an apparatus and method for treating fluid media by exposure to ultraviolet radiation. A fluid flow path from a fluid inlet to a fluid outlet is provided. The fluid flow path is proximate to a source of ultraviolet radiation. Reagents may be added to the system so that the reagent is present in the circulating fluid while the fluid is being exposed to the ultraviolet radiation. Samples of fluid may be withdrawn from the system so that process parameters may be adjusted. In a system in which the fluid flow path is defined by a plurality of interconnected pipes, a connecting means between the pipes includes a port through which reagent may be added or samples withdrawn from the system.

8 Claims, 2 Drawing Sheets

APPARATUS FOR TREATMENT OF FLUID MEDIA WITH ULTRAVIOLET IRRADIATION

BACKGROUND OF THE INVENTION

1. Field of the Invention

The present invention relates to a fluid media treatment apparatus and process. More particularly, the present invention relates to a fluid media treatment apparatus and process utilizing a combination of ultraviolet light and a chemical reagent, such as an oxidizing agent, to treat contaminated fluid media, reducing the total microorganism count as well as decreasing the level of non-biological pollutants in the fluid.

2. Description of the Prior Art

Ultraviolet systems for the treatment of biological pollutants in fluid are known in the art. Such systems have found utility in disinfecting waste water effluent, drinking water, swimming pools, hot tubs and spas, membrane desalting systems, in producing high purity water for electronics, pharmaceuticals, dairies, cosmetics, hospitals, laboratories and beverages, in aquaculture, for fish hatcheries, aquariums and marine parks, and in treating recirculating water in cooling towers. In these systems, the water is disinfected by exposing it to ultraviolet light from low pressure mercury lamps generating ultraviolet light of 254 nanometers.

In maximizing the efficiency of such known apparatuses, it has been known to control the flow pattern of the fluid media, the time of exposure to the ultraviolet light, lamp temperature, and to maximize the exposure of the fluid media to the ultraviolet light.

Some fluid media treatment systems employing ultraviolet light have immersed the ultraviolet light source in the fluid media. Others have maintained a flow of the fluid media through pipes in close proximity to the ultraviolet light source.

Commercial waste water treatment systems have employed pipes made of quartz or polytetraflouroethylene (sold under the trademark "TEFLON" by the E.I. duPont de Nemours & Co.), both of which are materials which efficiently pass ultraviolet light. Polytetraflouroethylene (PTFE) pipes have been particularly useful: they pass ultraviolet light, they are not fragile and because of their non-sticking properties, contaminants in the fluid do not stick to the sides of the (PTFE) pipes.

Alternative methods of treating waste water to kill microorganisms include chemical treatment through materials such as chlorine. In some commercial waste water treatment systems, chemical treatment has been conducted serially with ultraviolet treatment, with materials such as chlorine being added before or after the ultraviolet treatment.

Yet another system introduces air bubbles into the waste water.

SUMMARY OF THE INVENTION

It is an object of the present invention to decrease the levels of both biological and non-biological contaminants in fluid being treated.

It is a further object of the present invention to react non-biological contaminants in contaminated fluid media with oxidizing agents in the presence of a source of ultraviolet light.

It is a further object of the present invention to provide a fluid treatment system which provides for the introduction of a reagent into the flow of fluid proximate to the ultraviolet radiation source.

It is a further object of the present invention to allow for samples of fluid to be withdrawn from the fluid flow path for evaluation.

It is a further object of the present invention to allow process parameters to be adjusted depending upon the results of the evaluation of fluid samples.

It is a further object of the present invention to provide a connecting structure for pipes used in such a fluid treatment system which maintains the pipes in close proximity with the ultraviolet radiation sources and allows for both the withdrawal of fluid samples and for the introduction of a chemical reagent into the fluid flow path.

To fulfill the aforementioned objectives, the present invention provides both an apparatus and a process for treating fluid media by exposure to ultraviolet radiation. The apparatus includes a fluid media inlet and fluid media outlet. A plurality of spaced parallel pipes which are transparent to ultraviolet radiation are provided. The end of one pipe is connected to the fluid media inlet, and the end of another pipe is connected to the fluid media outlet. A continuous fluid flow path from the inlet to the outlet is provided by connecting the end of one pipe with the end of another pipe with a connecting means. The connecting means has a port in fluid communication with the fluid flow path. An ultraviolet radiation source is in close proximity with the pipes. Means for introducing a reagent into the fluid flow path through the port are also provided. Either alternatively or in conjunction with the means for introducing a reagent into the fluid flow path, means for withdrawing a fluid sample through the port are provided.

In the method of the present invention, a fluid media inlet, outlet and flow path are provided along with a source of ultraviolet radiation proximate to the fluid flow path. Fluid media is introduced into the flow path through the inlet and is circulated through the flow path. While the fluid is circulating, it is exposed to ultraviolet radiation from the ultraviolet radiation source. A reagent may be introduced into the fluid flow path between the fluid media inlet and outlet so that the reagent is present when the fluid media is exposed to the ultraviolet radiation. Alternatively or in conjunction with the introduction of the reagent, samples of the fluid may be drawn from the fluid flow path.

The present invention improves upon the prior art processes and apparatuses in serving additional functions: reacting with or oxidizing the non-biological contaminants in the fluid media while the fluid media is being exposed to the ultraviolet light; and, providing a port for the withdrawal of fluid samples during the ultraviolet treatment process. Thus, reactions which are catalyzed by heat or ultraviolet light may utilize the ultraviolet light sources present in the system: the ultraviolet radiation sources thus may serve a dual function in both killing microorganisms and in catalyzing the breakdown of non-biological contaminants. Furthermore, since fluid samples may be withdrawn during the treatment process, process parameters, such as flow rate and reagent level may be adjusted to an optimum level depending upon the level of contaminants in the sample.

DESCRIPTION OF THE ILLUSTRATED EMBODIMENT

Figure 1:
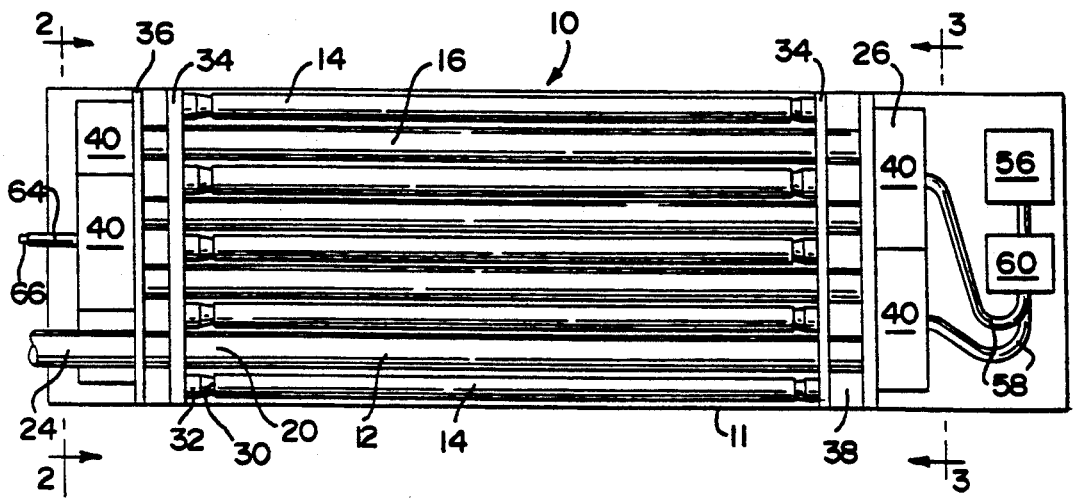
FIG. 1 is a top view of an fluid media treatment apparatus with its cover removed.

The present invention provides both an apparatus and a process for treating fluid media to decrease both biological and non-biological contaminants in the fluid media. It also provides for the withdrawal of samples from the system for evaluation and adjustment of process parameters. An illustrative fluid media treatment apparatus 10 is shown in FIG. 1. The illustrated apparatus is enclosed in a housing 11. As shown in FIG. 1, the housing's top cover is removed for illustration. The apparatus 10 provides a fluid flow path 12 through which the fluid media circulates. The fluid flow path is juxtaposed with a plurality of ultraviolet radiation sources 14. The apparatus provides for introducing a reagent into the fluid flow path proximate to the ultraviolet radiation sources so that the reagent is present in the circulating fluid media as the fluid media is exposed to the ultraviolet radiation.

In the illustrated apparatus, the fluid flow path 12 includes a plurality of spaced parallel pipes 16 arranged in overlying rows 20. An end of one pipe 16 is connected to a fluid media inlet 22, and the end of another pipe 16 in another row 20 is connected to a fluid media outlet 24. The pipes 16 in each row 20 and the rows 20 of pipes are interconnected to provide a continuous fluid flow path from the fluid media inlet, through each pipe in each row and through the rows of pipes to the fluid media outlet. In the illustrated embodiment, the pipes 16 are interconnected to define a serpentine path from the fluid media inlet 22 to the fluid media outlet 24.

To provide this continuous fluid flow path 12 through the pipes 16, means 26 are provided for connecting an end of one pipe to an end of another pipe. To provide a continuous fluid flow path through the pipes in each row, the connecting means 26 connects the end of one elongate pipe 16 to the end of an adjacent elongate pipe 16 in that row 20. To provide a continuous fluid flow path through the rows 20 of pipes 16, the connecting means 26 connects an end of one elongate pipe 16 in one row to the end of an adjacent elongate pipe 16 in an adjacent row 20. Thus, a continuous fluid flow path is provided from the fluid media inlet, through the pipes to the fluid media outlet.

As in some of the prior art systems, the fluid-carrying pipes 16 pass, that is, are transparent to ultraviolet radiation, and are preferably made of a sturdy material to which dirt and other contaminants will not adhere during processing. While quartz tubes will pass ultraviolet light, pipes made of polytetraflouroethylene (sold under the trademark "TEFLON" by E.I. DuPont de Nemours & Co.) are preferred because they are not fragile and because the contaminants in the fluid will not adhere to the sides of the pipes.

An illustrative support system for the ultraviolet radiation sources 14 is shown in the drawings. Support sockets 30 for the ultraviolet radiation sources 14, that is, germicidal radiation lamps, are mounted on vertical housings 32 which slide between the rows of pipes 16. Electrical leads (not shown) from the support sockets 30 may extend through the housings 32 and be connected to a suitable electrical power source (not shown) as will be understood by those of ordinary skill in the art. Apertured inner and outer support plates 34, 36 for the pipes 16 and connecting mean 26 may also be provided as shown in FIG. 1. The support plates 34, 36 may be separated to define isolated spaces 38 for the electrical wiring for the lamps 14. The pipes 16 extend through apertures in the plates 34, 36 and are connected to the connecting means 26 on the other side of the plate 36. The inner plates 34 may have supporting brackets (not shown) defining tracks within which the vertical housings 32 are held.

In the illustrated embodiment, the ultraviolet radiation sources 14 are low pressure mercury lamps generating ultraviolet light of 254 nanometers, close to the ideal of 260 nanometers for killing microorganisms. These germicidal lamps should provide an ultraviolet dosage of at least 6,000 to 10,000 microwatt seconds per square centimeter to destroy most microorganisms, such as coliform, staph and pseudomonas. An extra margin of safety may be provided by providing an ultraviolet light dosage of at least 30,000 microwatt seconds per square centimeter.

Depending upon the application, the microwatts per second of time and the time of treatment of the fluid, that is, the time of exposure to the ultraviolet light, may be varied. A system in a given application may require an ultraviolet dosage of 814,000 microwatts per second and longer treatment time to oxidize the contaminants in the fluid. The required optimum microwatts to oxidize the pollutants in the fluid should be determined on a case by case basis, since the optimum results will vary depending upon the reaction taking place in the fluid.

A plurality of ultraviolet radiation lamps 14 are provided in the illustrated embodiment, so that each pipe 16 is proximate to a lamp 14 on both sides of the pipe. Ideally, the exposure of the fluid in the pipes 16 is maximized by placing a plurality of lamps around the pipes and in close proximity to the pipes. The interior surface of the housing 11 may be made reflective to maximize the beneficial effects of the ultraviolet radiation.

Figure 2:
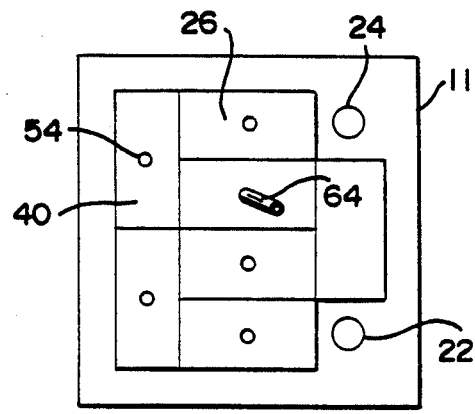
FIG. 2 is a view taken along line 2—2 of FIG. 1.

In the illustrated embodiment, the means 26 for connecting the ends of adjacent tubes and the means for connecting adjacent rows of tubes both comprise apertured blocks 40. As shown in FIG. 2, each block 40 has four rectangular faces 42 and two square end faces 44. Two adjacent parallel threaded bores 46 are provided in one face 42 of each block 40. A transverse bore 48 is perpendicular to and connects the adjacent parallel threaded bores 46. In the opposite face 42 of the block 40, a port 50 extends to the transverse bore 48. The port 50 is generally perpendicular to the transverse bore and parallel to the adjacent bores 46.

One threaded end of a pipe 16 is connected to one of the adjacent parallel threaded bores 46, and a threaded end of an adjacent pipe 16 in the row 20 is connected to the adjacent threaded bore 46 in the block 40. The connection between the pipe 16 ends and the adjacent bores 46 should be fluid tight, to prevent any leakage. Each of the adjacent parallel threaded bores has a diameter to match the diameter of the tubes, preferably about one inch. The adjacent parallel threaded bores are spaced apart about two to two and one-half inches, from center to center of the bores. Thus, a space of slightly greater than one inch will be left between the pipes 16. This spacing will allow an elongate ultraviolet radiation source 14, that is an elongate ultraviolet light tube, to be fit in between the pipes, while maintaining a very close spacing between the light tube and the pipes. This close spacing aids in maximizing the light exposure to the fluid in the tubes; preferably, the distance between longitudinal centerlines of an adjacent tube and light is less than 3 inches.

In addition, the illustrated embodiment provides abrupt changes in direction to increase the turbulence of the fluid flow. In these systems, turbulent flow is desirable because it increases the opportunity to expose the fluid to the ultraviolet light, so that dirt and other particulate matter within the fluid does not shield bacteria in the fluid from the ultraviolet radiation.

Figure 6:
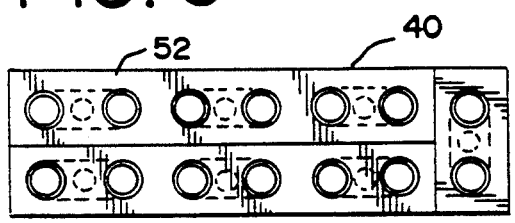
FIG. 6 is a front view of an alternative form of block useful with a fluid media treatment apparatus.

An alternative form of block is shown in FIG. 6. There, an elongate block 52 provides the necessary connection for six pipes. Other forms of blocks may be made within the scope of the invention.

The illustrated blocks 40, 52 are made of polypropylene because this material tends to be stand up under exposure to ultraviolet radiation. The blocks may be molded into the desired form, or the necessary bores 46, 48 and port 50 may be drilled into a solid block of polypropylene. If the bores 46, 48 are drilled into the solid block of polypropylene the transverse bore 48 may be drilled through from one of the square end faces 44 of the block to connect the adjacent bores 46. The open end of the transverse bore 46 may then be blocked off with a stopper.

The ports 50 in the blocks 40 serve a dual function: they allow for the introduction of chemical reagents into the fluid flow in the vicinity of the ultraviolet lights, and allow for withdrawing samples of fluid for selective testing of the fluid during processing to determine whether or not additional reagent is needed, to determine whether water temperature is at an optimum, and to provide other evaluations and treatments of the fluid. Depending upon the results of the evaluation of the fluid sample, these and other process parameters may be adjusted to optimum levels. Various structures may be employed in combination with the ports 50 to serve these two functions.

Figure 3:
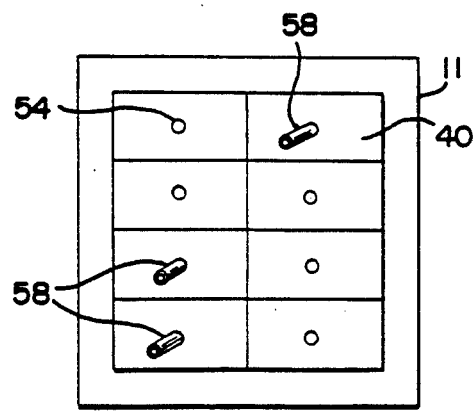
FIG. 3 is a view taken along line 3—3 of FIG. 1.
Figure 4:
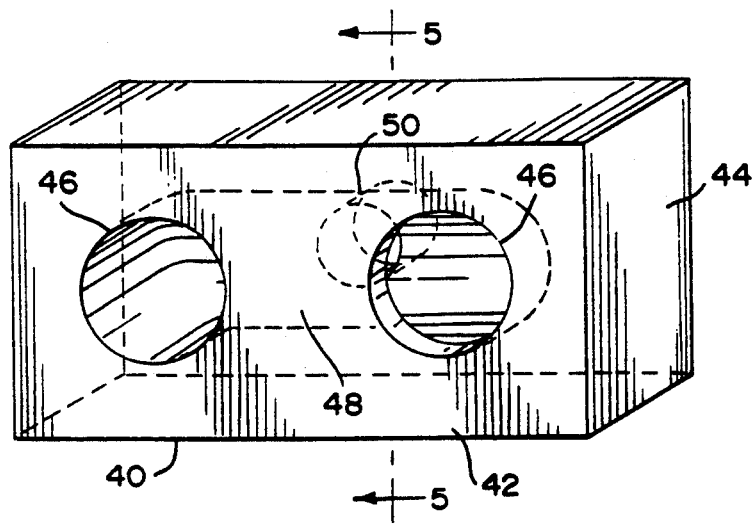
FIG. 4 is a perspective view of a block used to connect adjacent pipes in the fluid media treatment apparatus of FIG. 1.
Figure 5:
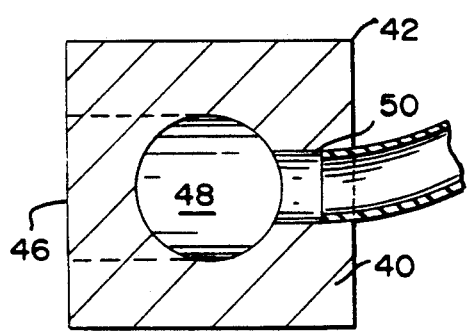
FIG. 5 is a cross-section of the block of FIG. 4 taken along line 5—5.

In the illustrated embodiment, a means for introducing a reagent into the fluid flow path 12 through the port 50 is provided, along with a means for withdrawing a fluid sample through the port 50 so that the fluid sample may be evaluated. It should be understood that either of these means may be used separately as well as in combination, and that a plurality of such means may be employed in one apparatus. It should also be understood that it is not necessary to connect such a means to every port; unused ports may be blocked with stoppers, as shown at 54 in FIGS. 2 and 3.

The illustrated means for introducing a reagent into the fluid flow path includes a reagent supply 56. The reagent may be an oxidizing agent, such as hydrogen peroxide or ozone. The reagent supply 56 is connected to the port 50 through a flexible conduit 58. A suitable bushing (not shown) may be used to hold the conduit 58 in place at the port 50. A pump 60 may also be used to deliver a predetermined level of reagent into the fluid flow. Depending upon the application, variations may be made in the illustrated set up. For example, a plurality of pumps may be used to deliver different quantities of reagent, to deliver reagent at different rates to different locations in the fluid flow path, or to deliver different reagents to different locations in the fluid flow path. Additional reagent supplies may be included to introduce additional reagents at different points in the process.

The illustrated means for withdrawing a fluid sample through the port 50 includes a conduit 64 connected to the port 50 through a bushing or other suitable structure (not shown) and valves or stop-cocks 66 for regulating the flow through and out of the conduits. By withdrawing fluid samples at different points in the system, the effectiveness of the treatment process and the need for more or less reagent may be monitored.

The particular reagent introduced into the system will depend upon the particular application, and may vary depending upon the nature of the contaminants in the fluid media. The amount of reagent used may vary with the level of contaminants in the fluid media, and the level and nature of contaminants may vary in a particular application over time. However, in general, it is expected that an oxidizing agent, such as hydrogen peroxide or ozone, will prove useful in decreasing the level of non-biological pollutants in the fluid media. Other oxidizing agents may also be used in the system of the present invention, and depending upon the particular application and the nature of the pollutants in the fluid, other reagents may also be utilized.

The contaminants found in most toxic ground water will vary greatly in their chemical compounds and in the strength of their solutions. Nature, with the help of sunlight (ultraviolet light) and oxygen (an oxidizer) in the air will, over an extended period of time, neutralize and/or oxidize these toxic compounds in the water. The system of the present invention utilizes the principles of this natural process, using ultraviolet light and a chemical oxidizer, and speeding up the natural process. The desired oxidation of chemical pollutants in fluid can be accomplished by applying the proper amount of ultraviolet light at a given wavelength and feeding and maintaining the proper amount of an oxidizer into the system.

Because the nature and concentration of the pollutants in a given fluid sample will vary considerably between facilities, and perhaps between fluid samples within a given facility, the desired ultraviolet light levels and types and amounts of reagent to treat the fluid will vary between facilities and over time within a given facility. Furthermore, the chemical compounds comprising the pollutants within a facility may vary. The present invention provides an effective mechanism for treating fluids in such variable systems, for it allows for periodic testing of the fluid samples at several points during the treatment process; it further allows for modification of the treatment process based through the introduction of different or additional oxidizers and reagents at several points during the treatment process. Thus, for example, a 35% solution of hydrogen peroxide in water may be used as an oxidizing agent, and in a particular application treating a fluid polluted with, for example, methylene chloride or chloroform, it may be desirable to maintain about 350 to 1000 parts per million of hydrogen peroxide, or at a ratio of about 14.25 to one (methylene chloride to hydrogen peroxide, by weight). However, the optimum ratio of reagent to pollutant, as well as the particular reagent used, will vary depending upon factors such as the particular pollutant and the concentration of that pollutant in the system.

In the method of the present invention, a fluid treatment system is provided having a fluid media inlet, a fluid media outlet, a fluid flow path between the inlet and the outlet, and a source of ultraviolet radiation proximate to the fluid flow path. The fluid media is introduced into the fluid media inlet 22 and the fluid media is circulated through the fluid flow path 12. As the fluid media circulates through the fluid flow path, it is exposed to ultraviolet radiation from the ultraviolet radiation source 14. A reagent may be introduced into the fluid flow path 12 between the fluid media inlet 22 and outlet 24 so that reagent is present in the fluid media as it is exposed to ultraviolet radiation. The reagent may be an oxidizing agent, and it may be hydrogen peroxide or ozone. Either in conjunction with the introduction of a reagent or separately, samples of the fluid may be withdrawn from the fluid flow path between the fluid media inlet and fluid media outlet. The samples may be evaluated and the amount of reactant or fluid flow rate through the fluid flow path may be adjusted based upon the evaluation.

If the method is used in conjunction with an apparatus having fluid carrying pipes interconnected with connecting means providing ports, the reagent may be introduced into the fluid flow path through such ports 50. If such ports 50 are provided, fluid samples may be withdrawn through these ports for evaluation.

Figure 7:
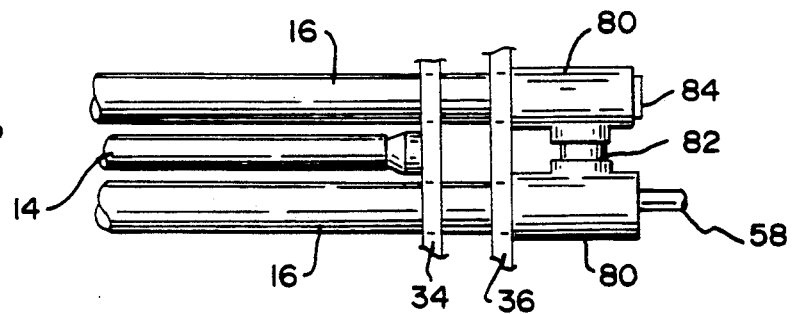
FIG. 7 is a partial top view of a fluid media treatment apparatus showing an alternative means for connecting the end of one pipe to the end of an adjacent pipe.
Figure 8:
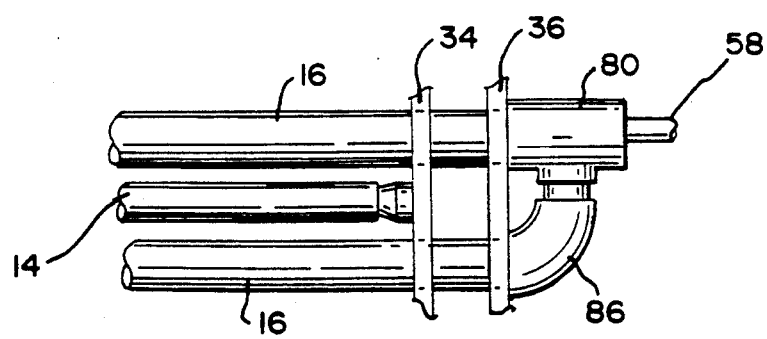
FIG. 8 is a partial top view of a fluid media treatment apparatus showing an alternative means for connecting the end of one pipe to the end of an adjacent pipe.

Many alternative structures to the illustrated blocks 40, 52 are available for the means for connecting the end of one pipe to the end of another pipe. For example, as shown in FIG. 7, a T-fitting 80 may be placed at the end of each pipe 16, with a short pipe section 82 extending between two T-fittings, each T-fitting having one end coaxial with and extending away from the pipes. These ends may be blocked with a suitable removable stopping means 84, which can be removed for access to the interior of the associated pipe, or connected through a flexible conduit 58 to the reagent supply as in the FIG. 1 embodiment. Similarly, as shown in FIG. 8, one T-fitting 80 may be used in combination with a single elbow joint 86 to provide the connection between adjacent pipes 16. Furthermore, should pairs of elbow joints be available to join the pipes while maintaining the pipes at the desired separation, such elbows may be used.

It should be understood that the apparatus and process of the present invention may be used in a wide variety of ultraviolet fluid treatment systems. The particular apparatus used may depend upon the application. For example, the number of pipes and therefore the length of the fluid flow path may vary with the particular application. It is not necessary that the particular arrangement of pipes and ultraviolet radiation sources shown in the drawings be employed. Furthermore, the process of the present invention may be used with systems which immerse an ultraviolet radiation source in the fluid flow path. Thus, although the invention has been described with respect to particular embodiments, it should be understood that the invention is not limited to that invention and is not limited to those embodiments. Additions or modifications may be made by those skilled in the art without departing from the scope of the invention as defined by the claims.

I claim:

1. An apparatus for treating fluid media by exposure to ultraviolet radiation, the apparatus comprising:

a fluid media inlet;
   a fluid media outlet;
   a plurality of spaced pipes substantially transparent to ultraviolet radiation, the end of one pipe being in fluid connection with the fluid media inlet and the end of another pipe being in fluid connection with the fluid media outlet;
   means for connecting the end of one pipe to the end of another pipe so that the pipes are in fluid connection to provide a continuous fluid flow path for carrying the fluid media from the fluid media inlet through the pipes to the fluid media outlet, the means for connecting the end of one pipe to the end of another pipe having a port in fluid communication with the fluid flow path;
   wherein the means for connecting the end of one pipe to the end of another pipe has adjacent bores for receiving the ends of adjacent pipes, two adjacent bores being connected by a transverse bore substantially perpendicular to the adjacent bores, and wherein the port is substantially perpendicular to and in fluid connection with the transverse bore; and
   an ultraviolet radiation source adjacent to the pipes; and
   means for introducing a reagent into the fluid flow path through the port.

2. An apparatus for treating fluid media by exposure to ultraviolet radiation as claimed in claim 1 wherein a plurality of ports are provided and further comprising means for withdrawing fluid through a port so that the fluid media may be evaluated.

3. An apparatus for treating fluid media by exposure to ultraviolet radiation as claimed in claim 1 wherein the means for introducing a reagent into the fluid flow path includes a supply of an oxidizing agent.

4. An apparatus for treating fluid media by exposure to ultraviolet radiation as claimed in claim 1 wherein the means for introducing a reagent into the fluid flow path includes a supply of hydrogen peroxide.

5. An apparatus for treating fluid media by exposure to ultraviolet radiation, the apparatus comprising:

a fluid media inlet;
   a fluid media outlet;
   a plurality of spaced pipes substantially transparent to ultraviolet radiation, the end of one pipe being in fluid connection with the fluid media inlet and the end of another pipe being in fluid connection with the fluid media outlet;
   means for connecting the end of one pipe to the end of another pipe so that the pipes are in fluid connection to provide a continuous fluid flow path for carrying the fluid media from the fluid media inlet through the pipes to the fluid media outlet, the means for connecting the end of one pipe to the end of another pipe having a port in fluid communication with the fluid flow path;
   wherein the means for connecting the end of one pipe to the end of another pipe has adjacent bores for receiving the ends of adjacent pipes, two adjacent bores being connected by a transverse bore substantially perpendicular to the adjacent bores, and wherein the port is substantially perpendicular to and in fluid connection with the transverse bore;
   an ultraviolet radiation source adjacent to the pipes; and
   means for withdrawing fluid through the port so that the fluid may be evaluated.

6. An apparatus for treating fluid media by exposure to ultraviolet radiation as claimed in claim 5 wherein a plurality of ultraviolet radiation sources are disposed substantially around the exterior of a plurality of the pipes and the port is disposed between the pipes substantially surrounded by the plurality of ultraviolet radiation sources.

7. An apparatus as claimed in claim 1 wherein a plurality of ultraviolet radiation sources are disposed substantially around the exterior of a plurality of the pipes and the port is disposed between the pipes substantially surrounded by the plurality of ultraviolet radiation sources.

8. An apparatus as claimed in claim 1 further comprising means for withdrawing fluid through the port so that the fluid may be evaluated.

* * * * *